US011906540B1

(12) United States Patent
Gwin et al.

(10) Patent No.: US 11,906,540 B1
(45) Date of Patent: Feb. 20, 2024

(54) AUTOMATIC DETECTION OF FALLS USING HYBRID DATA PROCESSING APPROACHES

(71) Applicant: BBY SOLUTIONS, INC., Richfield, MN (US)

(72) Inventors: Joseph Gwin, Concord, MA (US); Hyoki Lee, Lexington, MA (US); Ramin Oftadeh, Medford, MA (US)

(73) Assignee: BBY SOLUTIONS, INC., Richfield, MN (US)

( * ) Notice: Subject to any disclaimer, the term of this patent is extended or adjusted under 35 U.S.C. 154(b) by 0 days.

(21) Appl. No.: 17/515,086

(22) Filed: Oct. 29, 2021

Related U.S. Application Data

(60) Provisional application No. 63/108,039, filed on Oct. 30, 2020.

(51) Int. Cl.
*G01P 15/18* (2013.01)
*G06N 3/08* (2023.01)
*G01P 13/00* (2006.01)

(52) U.S. Cl.
CPC .............. *G01P 15/18* (2013.01); *G01P 13/00* (2013.01); *G06N 3/08* (2013.01)

(58) Field of Classification Search
CPC ............ G01P 15/18; G01P 13/00; G06N 3/08
USPC ........................................................ 73/865.4
See application file for complete search history.

(56) References Cited

U.S. PATENT DOCUMENTS

| 2017/0188895 | A1* | 7/2017 | Nathan ................. A61B 5/1118 |
| 2019/0325266 | A1* | 10/2019 | Klepper ................ G06F 18/214 |
| 2020/0013272 | A1* | 1/2020 | Hsu ..................... G08B 21/0446 |
| 2020/0211154 | A1* | 7/2020 | Ng ............................ G06N 3/08 |

FOREIGN PATENT DOCUMENTS

| WO | WO-2019157257 A1 * | 8/2019 | ............... G06N 3/04 |
| WO | WO-2020130924 A1 * | 6/2020 | ............... A61B 5/11 |

OTHER PUBLICATIONS

Abbate, Stefano, et al., "A smartphone-based fall detection system", Preprint submitted to Pervasive and Mobile Computing, (2012), 25 pgs.

(Continued)

*Primary Examiner* — Alesa Allgood
*Assistant Examiner* — Byung Ro Lee
(74) *Attorney, Agent, or Firm* — Schwegman, Lundberg & Woessner, P.A.

(57) ABSTRACT

Various approaches for automated fall detection, implemented in wearables and other device form factors of a personal emergency response system (PERS) are disclosed. In an example, a hybrid approach for fall detection includes: identifying a potential fall event from three-dimensional motion data of a human subject, using filtering rules; evaluating the motion data with a machine learning model (e.g., a decision tree ensemble (DTE) model), to produce a first determination that a fall has occurred; evaluating the motion data with a deep learning neural network (e.g., recurrent neural network such as a gated recurrent unit (GRU)), to produce a second determination that a fall has occurred; classifying the potential fall event as a fall condition for the human subject, based on the first determination and the second determination; and outputting data to indicate the fall condition for the human subject.

28 Claims, 9 Drawing Sheets

(56) References Cited

OTHER PUBLICATIONS

Abbate, Stefano, et al., "Recognition of false alarms in fall detection systems", 1st IEEE International Workshop on Consumer eHealth Platforms, Service and Applications, (2011), 23-28.

Bagala, Fabio, et al., "Evaluation of Accelerometer-Based Fall Detection Algorithms on Real-World Falls", PLoS ONE 7(5), (2012), 1-9.

Baig, Mirza M., et al., "A Systematic Review of Wearable Sensors and IoT-Based Monitoring Applications for Older Adults—a Focus on Ageing Population and Independent Living", Journal of Medical Systems, 43: 233, (2019), 11 pgs.

Casilari, Eduardo, et al., "Analysis of Public Datasets for Wearable Fall Detection Systems", Sensors, 17, 1513, (2014), 28 pgs.

Delahoz, Yueng S., et al., "Survey on Fall Detection and Fall Prevention Using Wearable and External Sensors", Sensors, 14, (2014), 19806-19842.

Gasparrini, Samuele, et al., "Proposal and Experimental Evaluation of Fall Detection Solution Based on Wearable and Depth Data Fusion", In: Advances in Intelligent Systems and Computing, vol. 399—ICT Innovations 2015, Loshkovska, S., et al., Editors, (2015), 99-108.

Kangas, Maarit, et al., "Sensitivity and specificity of fall detection in people aged 40 years and over", Gait & Posture, 29, (2009), 571-574.

Khojasteh, Samad B., et al., "Improving Fall Detection Using an On-Wrist Wearable Accelerometer", Sensors, 18, 1350, (2018), 28 pgs.

Kraft, Dimitri, et al., "Wrist-worn Accelerometer based Fall Detection for Embedded Systems and IoT devices using Deep Learning Algorithms", PETRA '20, Jun. 30-Jul. 3, 2020, Corfu, Greece, (2020), 352-361.

Leutheuser, Heike, et al., "Hierarchical, Multi-Sensor Based Classification of Daily Life Activities: Comparison with State-of-the-Art Algorithms Using a Benchmark Dataset", PLoS ONE 8(10): e75196, (2013), 1-11.

Luna-Perejon, Francisco, et al., "An Automated Fall Detection System Using Recurrent Neural Networks", International Conference on Artificial Intelligence in Medicine, (2019), 6 pgs.

Martindale, Christine F., et al., "Hidden Markov Model-Based Smart Annotation for Benchmark Cyclic Activity Recognition Database Using Wearables", Sensors, 19, 1820, (2019), 21 pgs.

Medrano, Carlos, et al., "Detecting Falls as Novelties in Acceleration Patterns Acquired with Smartphones", PLoS ONE 9(4): e94811, (Apr. 2014), 1-9.

Musci, Mirto, et al., "Online Fall Detection using Recurrent Neural Networks", arXiv:1804.04976v1 [cs.CY] Apr. 13, 2018, (2018), 6 pgs.

Ngu, Anne H., et al., "Smartwatch-Based IoT Fall Detection Application", Open Journal of Internet of Things, 4(1), (2018), 87-89.

Palmerini, Luca, et al., "Accelerometer-Based Fall Detection Using Machine Learning: Training and Testing on Real-World Falls", Sensors, 20, 6479, (2020), 15 pgs.

Putra, I Puta Edy S., "Towards a smart fall detection system using wearable sensors", Thesis, Coventry University and Macquarie University, (Mar. 2018), 259 pgs.

Reiss, Attila, et al., "Introducing a New Benchmarked Dataset for Activity Monitoring", 2012 16th International Symposium on Wearable Computers, (Jun. 18-22, 2012), (2012), 108-109.

Santos, Guto Leonii, et al., "Accelerometer-Based Human Fall Detection Using Convolutional Neural Networks", Sensors, 19, 1644, (2019), 12 pgs.

Wang, Changhong, et al., "Selecting Power-Efficient Signal Features for a Low-Power Fall Detector", IEEE Transactions on Biomedical Engineering, 64(11), (Nov. 2017), 2729-2736.

Yuan, Jian, et al., "Power-Efficient Interrupt-Driven Algorithms for Fall Detection and Classification of Activities of Daily Living", IEEE Sensors Journal, 15(3), (Mar. 2015), 1377-1387.

\* cited by examiner

US 11,906,540 B1

AUTOMATIC DETECTION OF FALLS USING HYBRID DATA PROCESSING APPROACHES

PRIORITY CLAIM

This application claims the benefit of priority to U.S. Provisional Patent Application No. 63/108,039, filed Oct. 30, 2020, which is incorporated by reference herein in its entirety.

TECHNICAL FIELD

The present disclosure relates generally to fall detection using body-worn sensors (such as wrist-worn sensors), and more particularly, to systems, devices, and methods for processing sensor data involving algorithms and models to identify such fall detection scenarios.

BACKGROUND

Falling is among the most serious health problems associated with aging. In recent statistics, falls are the leading cause of both fatal and nonfatal injuries among older adults (e.g., adults over 65 years). One in three older adults, and 75% of nursing home residents, will fall each year, with 20-30% of these leading to injuries. Lying on the floor for a long time after a fall is a major source of fall-related complications. Lengthy lie time can lead to kidney damage, pressure sores, hypothermia, dehydration, missed medication effects, and death. The risk of being unable to get up after a fall increases with age and declining muscle function.

A medical alert device (also called personal emergency response system or referred to as a "PERS") is a small wearable radio communication device that can be used to signal for help in the event of a fall. In one study, use of a PERS has been shown to reduce mortality rates by a factor of four and reduce hospital utilization by 59%. Unfortunately, the benefits of medical alert devices are limited by individuals not activating the alarm in the event of a fall. Another study has showed that among the "oldest old", 80% of individuals who had access to a PERS did not use it to call for help when they fell alone and could not get up. This was true in both institutional (94%) and community (78%) settings. As a result, various approaches have been attempted for automatic fall detection by personal devices, and for the automatic activation of help requests and alerts from the personal devices.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
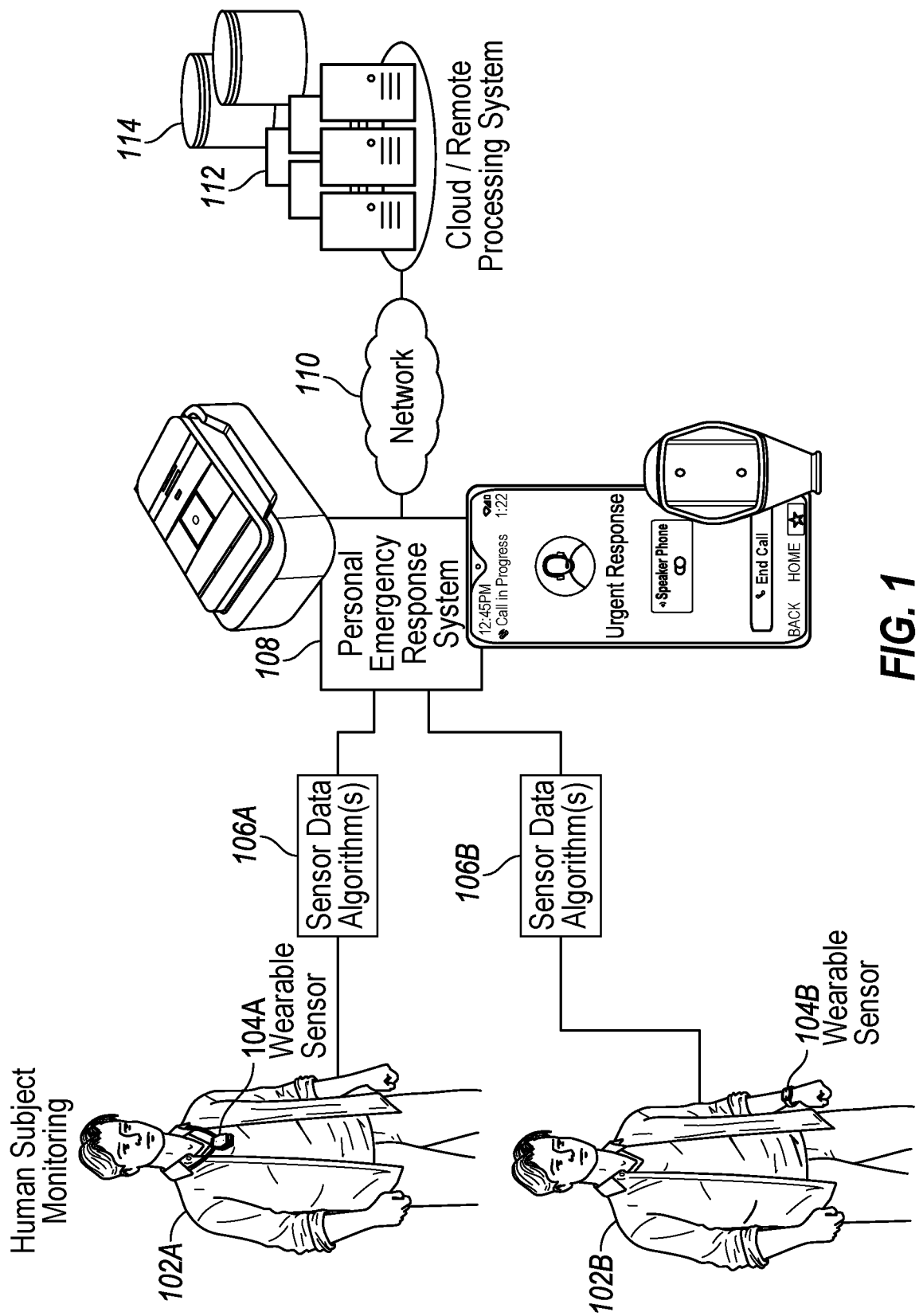
FIG. 1 illustrates a system for detecting falls, according to an example.

This document discusses various techniques, algorithms, and operations, applicable in fall detection devices and systems. Specifically, the present disclosure provides various systems, devices, and methods for detecting falls based on acceleration measured from a body worn sensor. In an example, a method for detecting falls is applied to sensor data collected from a tri-axial accelerometer of a sensor device worn on the wrist of a monitored human subject; however, the method is applicable to sensor data provided from a wearable device positioned on many other positions on the body, and from sensor data obtained or processed using other sensor types and device form factors.

As discussed herein, fall detection may be performed using a "hybrid model" approach. In an example, this hybrid model combines the computational efficiency of a Decision Tree (DT) approach with the increased accuracy (and relatively higher computational cost) of a Deep Learning model. The determination of falls with this hybrid model may also be controlled based on the application of specific rules, thresholds, time-based events, and post-processing evaluation, to decrease the chances of false positives. Related approaches and embodiments applicable to personal emergency response system (PERS) implementations and other fall detection features in electronic devices and systems are also disclosed.

PERS with automatic fall detection can signal for help if the wearer forgets to, or is incapable of, pressing an alert button when a fall occurs. One example implementation of automatic fall detection and alerting in a PERS is provided from the automatic fall detection algorithm embedded in the Lively Mobile and Lively Wearable PERS offerings from Lively (Best Buy Health, Richfield, Minnesota, USA). This and other PERS designs may include use of an automatic fall detection algorithm based on sensors attached to the chest or worn as a pendant.

With the prevalence of wrist-worn smart devices and activity trackers, there has been a shift in customer preference towards wrist-worn PERS; however, appropriate technology solutions are lacking. For example, consider the current state of fall detection algorithms incorporated with use of wrist-based devices. Even the best fall detection algorithms that are tested on real-world laboratory falls, simulated falls, and simulated activities of daily living (ADLs), are only capable of yielding a sensitivity between 90-95 percent, and an error rate of around five percent. Likewise, some smart watches with fall detection features explain that the algorithms used in these devices detect only "hard falls", and come with a disclaimer that the algorithms may not detect all falls and that false alarms are more likely for more those who are more physically active.

The following discloses features of an automatic fall detection algorithm and implementation usable by wrist-worn devices containing a tri-axial accelerometer or similar sensor components. The following contrasts three different computational methods to develop an automatic fall detection algorithm, based on accelerometer data. The computational methods compared are Decision Tree Ensemble (DTE), Gated Recurrent Unit (GRU), and a hybrid combination of DTE and GRU. The hybrid combination presented herein represents a significant step forward in the accuracy and reliability of automatic fall detection for wrist-worn PERS.

In particular, the following hybrid combination of DTE and GRU enables a data processing algorithm to be processed in real-time on a wearable device. Unlike prior approaches which have experimented with use of a deep learning algorithm such as GRU, the following enables implementation of a fall detection algorithm directly on a wearable device, without requiring processing by an external device or system such as a phone, a tablet, a hub, a cloud processing system, and the like.

Additionally, the GRU model, as implemented in the following example of the hybrid combination, may be used without needing to repeatedly run the GRU model on every data sample that is collected. For instance, the GRU model may be used to evaluate data only when a DTE algorithm determines the potential fall event as a fall, such that the GRU model can make a final decision (classification) on the sensor data.

A variety of implementation changes and variations to the GRU and DTE models may be enabled by the present hybrid model. For instance, the following examples include a GRU model that may be implemented within a wearable device for real-time processing, after optimizing the GRU model network with quantization and the creation of look-up tables for several activation functions (i.e., hyperbolic tangent, sigmoid, and exponential operations). This enables a smaller GRU model to be implemented and stored directly on the device, even with limitations on the memory space and computational timing provided by the wearable circuitry. These and other advantages over prior approaches and implementations will be apparent from the following description.

FIG. 1 illustrates, by way of example, a schematic overview of a fall detection system. As shown, a human subject 102 (e.g., patient) utilizes a sensor device 104 (e.g., by wearing the device, or by wearing an apparatus or component coupled to the sensor device) in order to collect relevant sensor data. The fall detection system applies one or more algorithms 106 on the sensor data captured by the sensor device 104. A personal emergency response system (PERS) 108 calculates or considers the results of the sensor data algorithms 106 and provides alerts when a fall is detected for the human subject 102. The PERS 108 may be integrated into the sensor device 104, provided as a function of an electronic device (e.g., as a function operating within a smartphone, watch, etc.), or operated as part of a medical device, monitoring device, or other electronic system.

A first example of a sensor device 104 is provided with reference to a wearable sensor device 104A in the form of a pendant, which is worn by the human subject 102A. A second example of a sensor device 104 is provided with reference to a wearable sensor device 104B in the form of a smartwatch. In an example, either form of the wearable sensor device 104A, 104B includes an accelerometer (e.g., a tri-axial accelerometer) which provides simultaneous measurements in three dimensions or planes (x, y, z directions). Other motion and orientation sensors such as a gyroscope, magnetometer, or inertial measurement unit may also be incorporated into the sensor device 104.

In various examples, the sensor device 104, the sensor data algorithms 106, and the PERS 108 may be jointly or separately integrated into wearable form factors such as a watch, bracelet, pendant, clothing, or the like; or integrated with other electronic equipment such as a smartwatch, smartphone, or other user interface or communication apparatus. A variety of circuitry including processing circuitry, memory circuitry, solid state storage circuitry (not shown) may be used to implement the sensor data algorithms 106, collect data from the accelerometer and other sensors, execute logic associated with fall detection and fall alert features of the PERS 108, and the like.

The PERS 108 may include or interact with a user interface which is used to provide fall detection alert, warning, or logging functions. For example, a PERS 108 may be implemented by specialized software executing on a smartphone, which receives a wireless alert (e.g., Bluetooth or Wi-Fi communication) from the wearable sensor 104. The PERS 108 may perform functions such as making a phone call (e.g., to an emergency rescue service, to a trusted contact, etc.), sending an electronic communication (e.g., text message), or the like. A PERS 108 which is integrated into features of a cellular or Wi-Fi connected smartwatch or smart device may perform such communication operations directly via a network 110 connection.

The PERS 108 may communicate with a local or remote processing system to communicate an alert status, an alarm or alert condition (e.g., an identified fall condition), a device status, logging data, monitoring data, and the like. In an example, the PERS 108 communicates with a cloud remote data processing system 112 to initiate, provide, control, or evaluate alert actions. The cloud remote data processing system 112 utilizes a data store 114 (e.g., a data warehouse, database system, etc.) for the retrieval, access, persistence, and entry of data values. For instance, data relating to fall detection events, false alarms, user-initiated alerts, user feedback or controls, or the like may be communicated to and stored in the cloud remote data processing system 112 and the data store 114. In some examples, the cloud remote data processing system 112 may also perform validation of sensor data and of alerts or alarm conditions.

The PERS 108 may coordinate a variety of fall data collection and aggregation operations, including the selection and execution of specific fall detection algorithms. In an example, training and testing of fall detection algorithms may be based on diverse data and datasets. Thus, such fall detection algorithms may be tuned and validated in order to increase sensitivity (e.g., the algorithm's ability to correctly identify actual fall events, i.e., to increase the rate of true positives) while also increasing specificity (e.g., the algorithm's ability to correctly identify non-fall events, i.e., to increase the rate of true negatives), even as there is often a tradeoff between these two values.

In an example, algorithms may be tuned, adjusted, trained, or validated based on data and datasets relating to: (a) falls and activities of daily living (ADLs); (b) scripted tasks collected in a laboratory environment, including simulated falls and/or simulated ADLs; and (c) unscripted activities, "true ADLs", collected during daily life. Such data and datasets may be based on data collected from multiple wearable areas (e.g., both the left and right wrist), and treating such data were treated as independent samples. For example, the selection of tri-axial acceleration data may be provided from a collection of data from sensor devices worn on one or both wrists and sampled at a frequency of 50 Hz or greater. In another example, sensor data used for training or validation of algorithms may be collected from placements provided from among: Waist (including left or right side of waist); Right Pocket; Left Wrist; Right Wrist; Dominant wrist; Left Foot; Right Foot; Ankle; Chest. It will be understood that the sensors discussed herein may be adapted for placement or use on any of these areas.

Also for example, sensor data used for training or validation of algorithms may be based on activity types such as: Grasping; Laying; Sit; Walking; Jogging; Running; Sidestep; Jump; Hopping; Skipping; Ascending/descending stairs; Rest; Sleeping; Sit Cycle; Sitting; Lying; Standing; Working at a desk; Eating; Washing dishes; Vacuuming; Cleaning; Ironing; Sweeping; Ascending stairs; Descending stairs; Treadmill running; Bicycling; Rope jumping; Nordic walking; Exercising; Performing Yoga poses; and the like. In these and other contexts, specific fall events may be identified or classified in connection with training or validation of algorithms. Such fall types may be categorized as: Falling Back; Falling, ending up lying back: falling, ending up Sitting Front; Falling to side. More specific examples of such falls may include: 1) falling forward unbroken; 2) falling forward in two phases (fall onto knees first); 3) falling forward, twisting, and coming to rest in a supine position; 4) falling forward during a sit-to-stand transition; 5) falling forward during rising up from bed; 6) falling forward after descending stairs and missing the last step; 7) falling backward during a step up; 8) falling backward unbroken; 9) falling backward during rising after picking up something from the floor; 10) falling backward while trying to sit down; 11) falling laterally ending in a supine position; 12) falling laterally ending in a prone position; 13) falling laterally ending with lying laterally; 14) falling laterally from a chair; 15) collapse, ending with lying laterally.

Other examples of fall scenarios trained from ADLs may include: 1) bending down and then standing up; 2) walking at a normal speed; 3) sitting down in a normal chair; 4) sitting down in a deep chair; 5) standing up; 6) lying on a bed; 7) getting up from a bed; 8) changing postures during lying; 9) walking at a slow speed; 10) walking at a fast speed. Other variations of these movement tasks, including at different speeds and while performing activities (e.g., walking up and down stairs) may also be provided. Thus, it will be understood that variations to test subjects, test trials, test scenarios, monitoring sensors, and monitoring sampling rates may be used for training and validation data sets.

Figure 2:
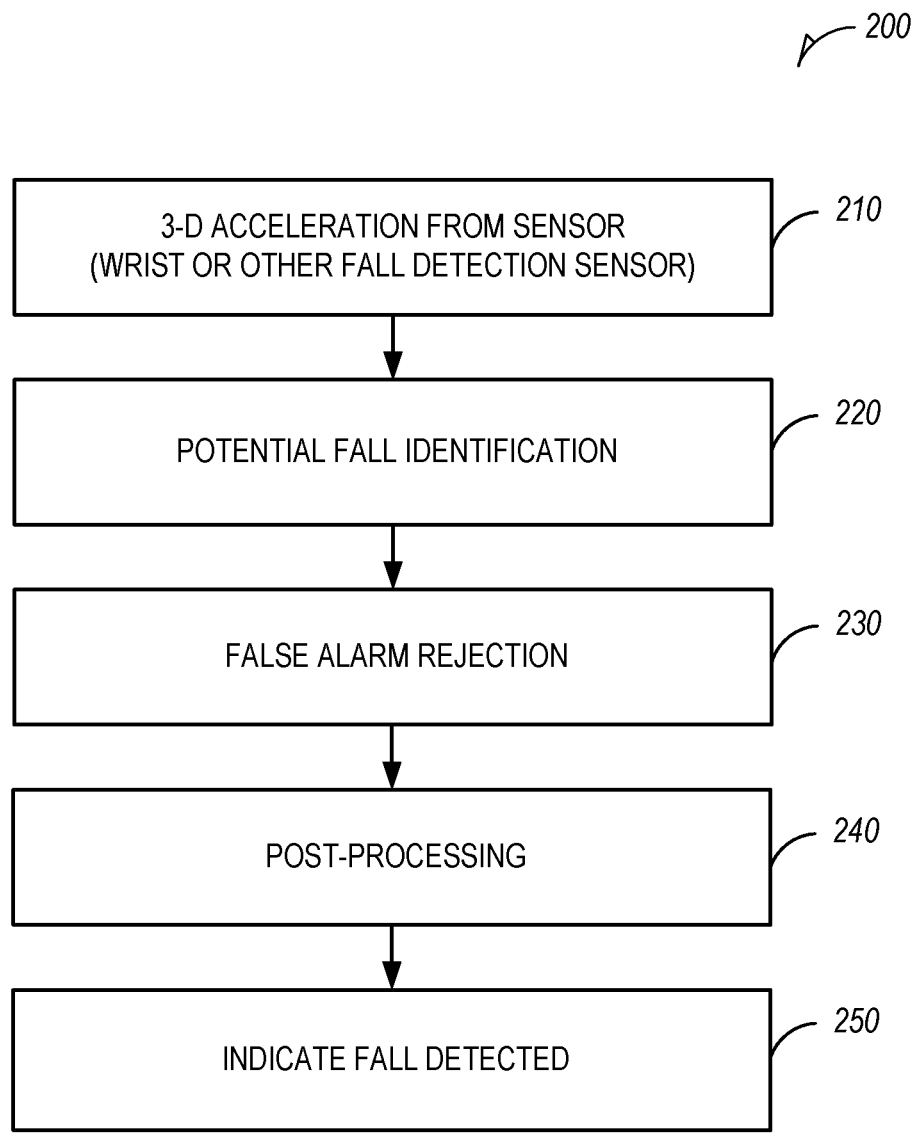
FIG. 2 illustrates a flowchart of an example data processing pipeline, according to an example.

In an example, a sensor data algorithm pipeline includes one evaluative procedure for identification of potential falls, followed by two evaluative procedures which reject false alarms. This is depicted in the flowchart of FIG. 2. A first operation (operation 210) is performed to collect data from 3D acceleration on a sensor device (e.g., a wrist sensor); this acceleration data may be downsampled (e.g., to 50 Hz) and fed into the algorithm pipeline. Second, an operation identifies potential falls (operation 220) using a set of simple rules, such as adapted from algorithms previously deployed for fall detection using pendant or wrist worn devices. Third, an operation is performed for false alarm rejection (operation 230), such as by feeding a short window of acceleration data surrounding each potential fall each one of two machine learning techniques which classify falls versus non-falls. Fourth, a post-processing operation is performed (240) to analyze all identified falls in their original context to reject cases in which the subject recovers (e.g., demonstrated by the detection of walking activity in the 20 seconds immediately following the fall). Based on the data analysis, a detected fall condition may be signaled (operation 250) or not signaled.

Additional details of potential fall identification (operation 220), false alarm rejection (operation 230), and post-processing (operation 240) are provided in the following paragraphs. It will be understood that a variety of approaches for collecting 3-D acceleration data (operation 210) from an accelerometer or other types of sensors, and a variety of approaches for responding to a detected fall or the non-detection of a fall (operation 250) may be incorporated into this system.

In an example, potential falls are identified (e.g., with operation 220) using a rule-based algorithm. Broadly speaking, the rules of a rule-based algorithm consider acceleration, velocity, and variability of the motion surrounding the impact event. Such rules may be designed and identified experimentally. This rule-based algorithm operates as a filter, to reduce the volume of data that needs to pass through the more computationally heavy portion of the algorithm pipeline, discussed below.

False alarm rejection (e.g., with operation 230) may be implemented with machine learning algorithms. In an example, after identifying potential fall events with the rule-based algorithm, false alarms are rejected using each of two different machine learning techniques: decision tree ensemble (DTE) and gated recurrent unit (GRU). These techniques have been separately researched for use with fall detection algorithms for sensors worn on the body, but are considered in existing literature as mutually exclusive approaches for event classification.

A decision tree is a sequence of binary feature evaluations used for decision support. In the present example, ensemble learning is used to combine several decision trees into a DTE to produce better predictive performance. For instance, a DTE model may be trained using Bayesian optimization for hyperparameter tuning and feature selection. Bayesian optimization for the DTE model can reduce the number of features that were initially identified into a much smaller set that are included in the model. Thus, the amount of data needed for operating and using the DTE can be reduced, having significant advantages on wearable devices with constrained computation and memory capabilities.

A GRU model is a type of artificial neural network that has feedback connections, enabling it to handle sequences of time-series data. To train the GRU model, acceleration data around the impact peak can be labeled as a fall while all other data is labelled as a non-fall. A trained GRU model then can be optimized using data augmentation, down-sampling of data, and varying the number of GRU layers. Imbalances in quantity of fall and non-fall data can be compensated for by adjusting class weights in GRU training, as discussed in more detail below.

The present hybrid approach for false alarm rejection is established by combining results of the DTE and GRU models. GRU is more computationally heavy and at the same time more accurate than DTE. Therefore, in the hybrid approach, potential falls from the DTE model are fed to the GRU for further evaluation. In an example, the output of the DTE, GRU, or hybrid model is an estimate of the probability that an event (e.g., potential fall identified by the rule-based algorithm) is a true fall. By setting a probability threshold, each event can then be classified as fall or non-fall.

The post-processing of each potential fall event (operation 250) may be performed by assessing the potential fall event in-context. For instance, if walking is detected within a period of 20 seconds after the fall event, the event can be reclassified as a non-fall, and no emergency alert would be transmitted in this case. Other post-processing scenarios can be used to clear alerts, offer warnings or clearable events to users, or to re-categorize events or sensor data classifications.

Evaluation of algorithm performance may be provided using any number of validation standards. In one example, sensitivity and false alarm rate of an algorithm instance may be calculated with comparison of a receiver operator characteristic (ROC). Results are typically represented as a ROC curve that shows sensitivity on the vertical axis and 1-specificity on the horizontal axis.

In the case of fall detection, or any algorithm triggered by threshold crossing in continuous timeseries data, the definition of a true negative is arbitrary (by lowering the threshold the number of true negatives increase towards infinity) and, therefore, specificity is not necessarily a meaningful performance metric. The more meaningful metric to be evaluated is the false alarm rate, which is defined as the number of false positives per unit of time. To represent real-world performance, false alarm rates may be validated using data from true ADLs (e.g., data collected during unscripted daily living). For datasets that do not include sleep, daily false alarm rates may be computed assuming a 16-hour day instead of a 24-hour day. This removes the bias of active hours and maintains the balance between active and inactive hours assumed to take place in a 24-hour period.

As can be illustrated with ROC graphs, DTE versus GRU models offer performance versus implementation tradeoffs. The DTE model requires the least memory and fewest number of computations to execute. It also provides results that are easily interpretable. Importantly, DTE models can easily be implemented in fixed-point embedded code. On the other hand, the GRU model performs better but uses notably more memory and is computationally more expensive than DTE. However, one way to reduce the memory size and computational effort of the GRU is to quantize the model weights and create a lookup table for activation functions in the network. By quantizing the network weights, the computational effort can be decreased by four-fold without losing the model performance.

More details about optimizations offered for both DTE and GRU models are provided throughout the present disclosure. As one example, to evaluate the trade-off between sensitivity and false alarm rate, a probability threshold can be adjusted, such as with the probability threshold that is used to convert the machine learning output to a binary classification (e.g., fall or non-fall).

Accordingly, a hybrid model (which is a combination of DTE and GRU models) offers a best-performing approach for an evaluative data scenario. Such a hybrid model may yield high sensitivities while maintaining low false alarm rates. This hybrid approach outperforms any wrist-based fall detection algorithm currently available in the literature and represents a significant step forward in the ability to detect falls accurately and reliably especially for elderly subjects.

Figure 3:
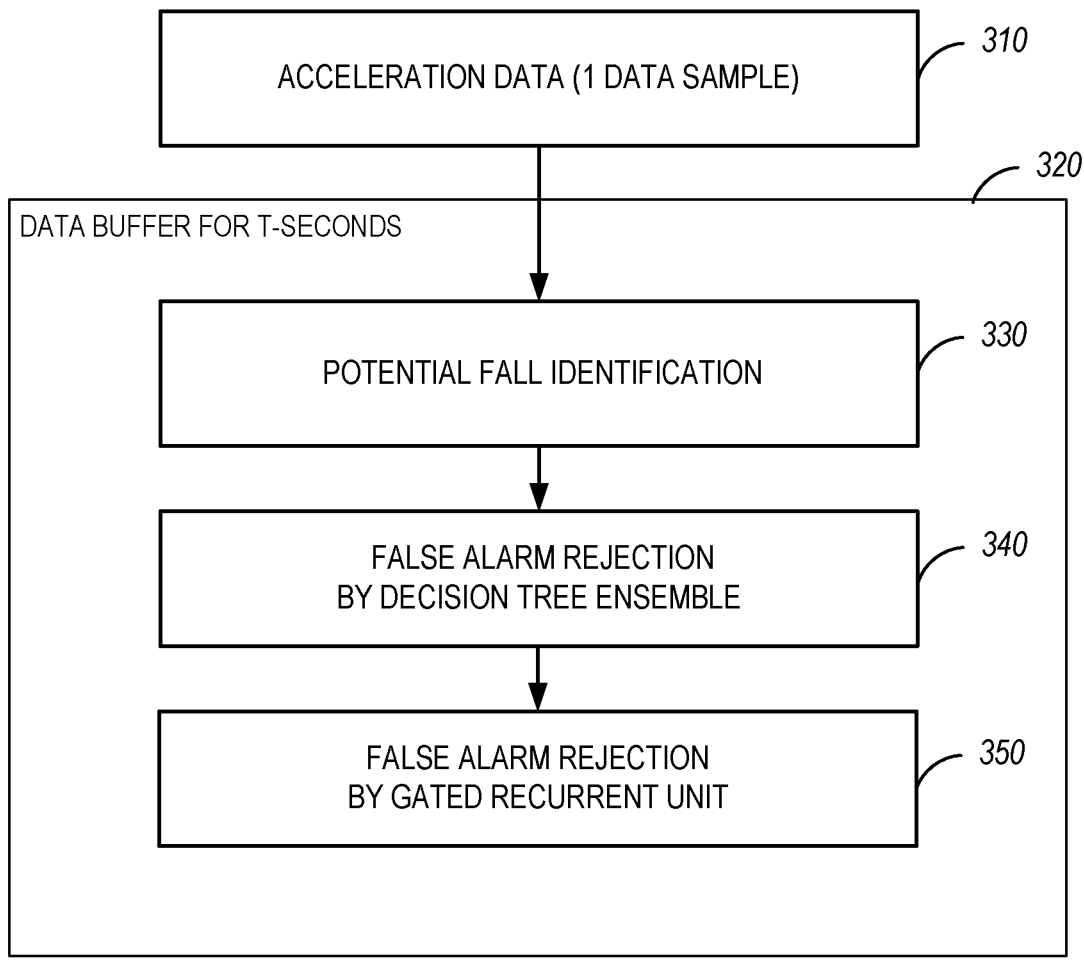
FIG. 3 illustrates a flowchart of an algorithm pipeline for potential fall identification and false alarm rejection, according to an example.

FIG. 3 illustrates a flowchart of an algorithm pipeline for potential fall identification and false alarm rejection. Here, this architecture involves the sequential analysis of acceleration data (e.g., three-dimensional motion data of a human subject), obtained from an accelerometer.

First, an acceleration data sample 310 is provided for processing using a data buffer 320. In an example, the acceleration data sample is a single data sample of three-dimensional acceleration (x, y, z) [1×3]. This data sample 310 is illustrated as sample 411, 421, 431, 441, with reference to FIG. 4.

The data buffer 320 is used to obtain multiple data samples of 3-D acceleration [N×3] (N=T× (sampling rate)). In this formula, T indicates the time duration of the buffer (e.g., T=4 seconds) which may be adjusted. N is the size of the buffer (e.g., N=400 at the sampling rate of 100 Hz). This data buffer 320 is illustrated as buffer data sets 412, 422, 432, 442 with reference to FIG. 4.

Figure 4:
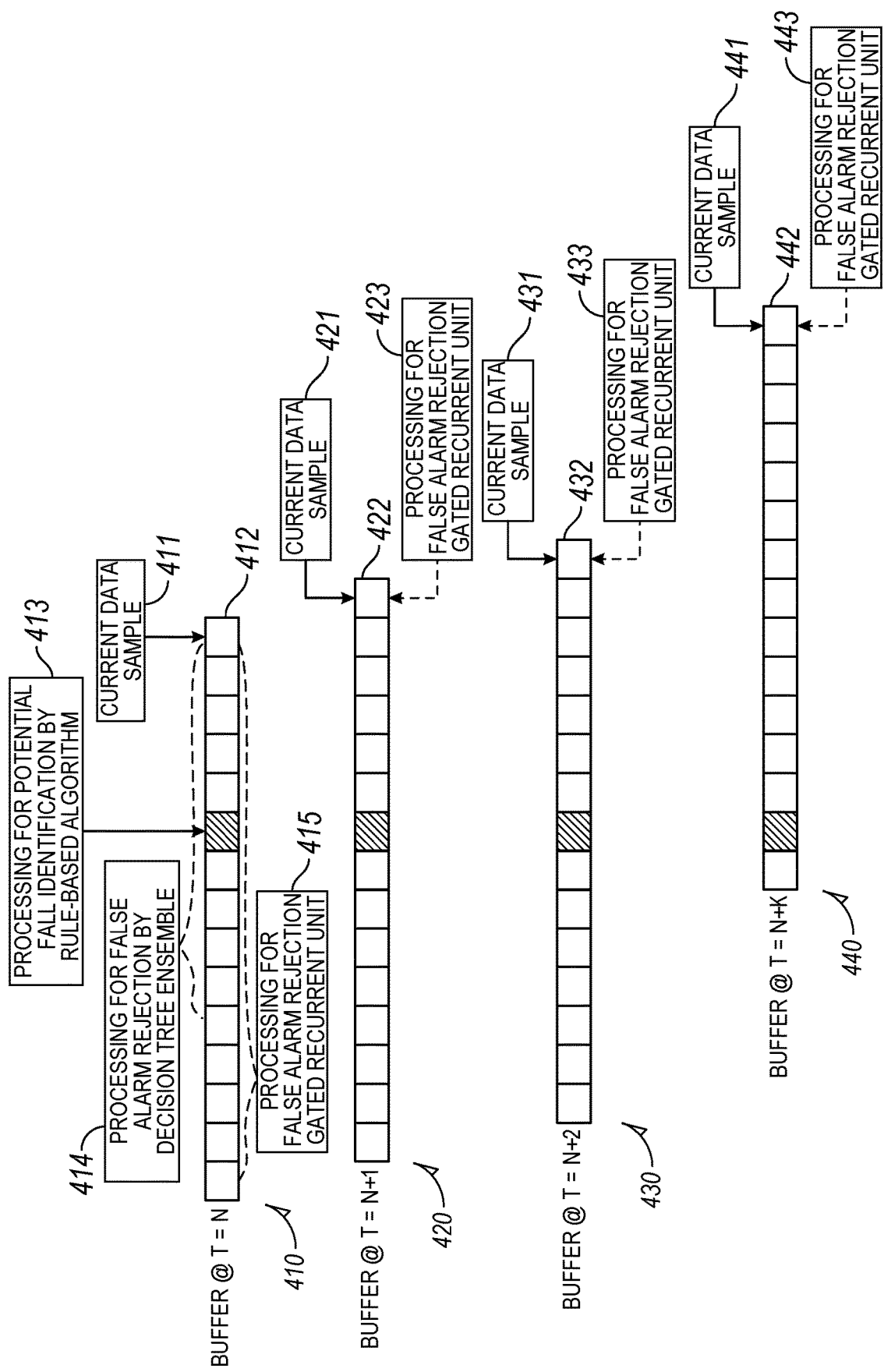
FIG. 4 illustrates data processing sequences for potential fall identification and false alarm rejection, according to an example.

Within the algorithm pipeline, a first operation performs an identification of potential falls using a rule-based algorithm at process 330. This process 330 is used to identify potential fall using one or more rules implemented by the rule-based algorithm. For instance, the rules consider acceleration, velocity, and variability of the motion surrounding the impact event. The purpose of this process 330 is to reduce the volume of data that needs to pass through the more computationally heavy portion of the algorithm pipeline. The process 330 is depicted with operation 413 in FIG. 4. In FIG. 4, the shaded box indicates that a potential fall event is identified in a data sample by the rule-based algorithm. The process 330 may be repeatedly continued for ongoing fall identification, regardless of whether a false alarm rejection is being processed or not.

Next, in the algorithm pipeline, a second operation performs a false alarm rejection using a DTE model at process 340. This process 340 is activated when a potential fall is identified (e.g., from process 330). The decision tree (DT) is a sequence of binary feature evaluations used for decision support. In an example, ensemble learning is used to combine multiple decision trees to produce better predictive performance. For instance, a DTE model may be trained using Bayesian optimization for hyperparameter tuning and feature selection. The process 340 is depicted with operation 414 in FIG. 4.

Next, in the algorithm pipeline, a third operation performs a false alarm rejection using a GRU model at process 350. This process 350 is activated when a potential fall is identified but not rejected by the DTE. In other words, the GRU model does not need to be initiated and executed repeatedly or all the time, but is only triggered on specific scenarios triggered by the DTE. This is depicted with operations 415, 423, 433, 443 in FIG. 4.

As will be understood, GRU is more computationally heavy and at the same time more accurate than DTE. However, the size of memory allocation and the processing time for GRU processing in the firmware of the executing device (i.e., a wearable device) can be reduced by the network quantization. A reduced memory allocation also may be provided from optimization of the GRU model as follows.

FIG. 4 illustrates data processing sequences 410, 420, 430, 440 for potential fall identification and false alarm rejection. Here, these sequences illustrate scenarios of data processing when the GRU processing is invoked (i.e., a potential fall has been identified by the rule-based algorithm and the DTE model has not rejected the potential fall). In each of the depicted scenarios of FIG. 4: t indicates current sample time; n indicates the sample time when a potential fall is identified; k indicates the end of the sample time for GRU processing.

First, referring to sequence 410, a current acceleration data sample (x[n], y[n], z[n]) 411 is entered to the buffer 412. The state of the buffer 412 is shown at t=n. At operation 413, the rule-based algorithm is used to determine whether there is a potential fall event at a certain number of samples (e.g., t−p) prior to the current data sample point (i.e., shaded area). At operation 414, If the potential fall event is identified, the DTE model processes data from (t−2×p+1) to (t−p) to determine whether the potential fall event should be rejected as a false alarm or not. At operation 415, if the potential fall event is not rejected by the DTE model, the GRU model processes data from (t−N+1) to t to determine whether the potential fall event should be rejected as a false alarm or not. If the GRU model determines that the potential fall event is a true fall, then the GRU processing is terminated, and a fall condition will be triggered. If the GRU model does not determine that the potential fall event is a true fall by t, the GRU model processing will be continued until (n+k) (e.g., shown in buffer 442, discussed below).

Next, referring to sequence 420, a new acceleration data sample (x[n+1], y[n+1], z[n+1]) is entered to the buffer 422. The state of the buffer 422 is shown at t=n+1 (with the oldest data sample being removed). At operation 423, the GRU model is processed using the new acceleration data sample only. If the GRU model determines that the potential fall event is a true fall, then the GRU processing is terminated, and a fall condition will be triggered. If the GRU model does not determine that the potential fall is a true fall, the GRU processing will be continued until (n+k) (e.g., shown in buffer 442, discussed below).

Next, referring to sequence 430, a new acceleration data sample (x[n+2], y[n+2], z[n+2]) is entered to the buffer 432. The state of the buffer 432 is shown at t=n+2 (with the oldest data sample being removed). At operation 433, the GRU model is processed using the new acceleration data sample only. If the GRU model determines that the potential fall event is a true fall, then the GRU processing is terminated, and a fall condition will be triggered. If the GRU model does not determine that the potential fall is a true fall, the GRU processing will be continued until (n+k) (e.g., shown in buffer 442, discussed below).

Next, referring to sequence 440, a new acceleration data sample (x[n+k], y[n+k], z[n+k]) is entered to the buffer 442. The state of the buffer 442 is shown at t=n+k (with the oldest data sample being removed). At operation 443, the GRU model is processed using the new acceleration data sample only. If the GRU model determined that the potential fall event is a true fall, then the GRU processing is terminated. If the GRU model has not determined the potential fall as a true fall, the GRU model determined that the potential fall event is a false alarm and the GRU processing is terminated. k could be expanded if another potential fall is identified in the middle of GRU processing. If another potential fall is identified at t=n+s, the GRU processing will be terminated at (t=n+k+s). However, k cannot be expanded to the infinite so the k should be restricted at the pre-defined threshold. (e.g., s≤2000=20-second×100-sample).

In the examples above, the GRU processing is performed when the DT model did not reject the potential fall event. Since the GRU processing requires a heavy memory space and computational effort in the wearable device processor, the size of GRU can be diminished effectively without losing the algorithm performance. For example, the GRU model includes 30,000 weights (i.e., model coefficients) with hyperbolic tangent, sigmoid, and exponential operations which are computationally expensive for determining whether the potential fall event is true or false.

In an example, to run the GRU model process with a constrained wearable device processor, a GRU model design may be adapted with following characteristics:

1) The network quantization technique is used to reduce the number of weights (e.g., to a number up to 1,000).

2) A look-up table is used for the activation functions including hyperbolic tangent, sigmoid, and exponential operations which cannot implemented directly to the device processor. The look-up table may be created by simulating a dataset collected internally and externally.

3) The matrix multiplications in the model may be converted to the look-up table.

Combination of these three techniques can enable execution of the hybrid fall detection algorithm in the wearable device in real-time. The size of GRU layers or the size of the look-up tables may be adjusted according to the target of the algorithm performance. As will be understood, there are tradeoffs when the size of the GRU layers is increased. Larger layers can improve the performance of the model but on the other hand the computational time and memory footprint will be increased. In the hybrid algorithm processing depicted in FIG. 4, the GRU processing is performed on every data sample. Therefore, determining the appropriate size of the GRU weights and the look-up tables is critical for optimal performance.

Figure 5:
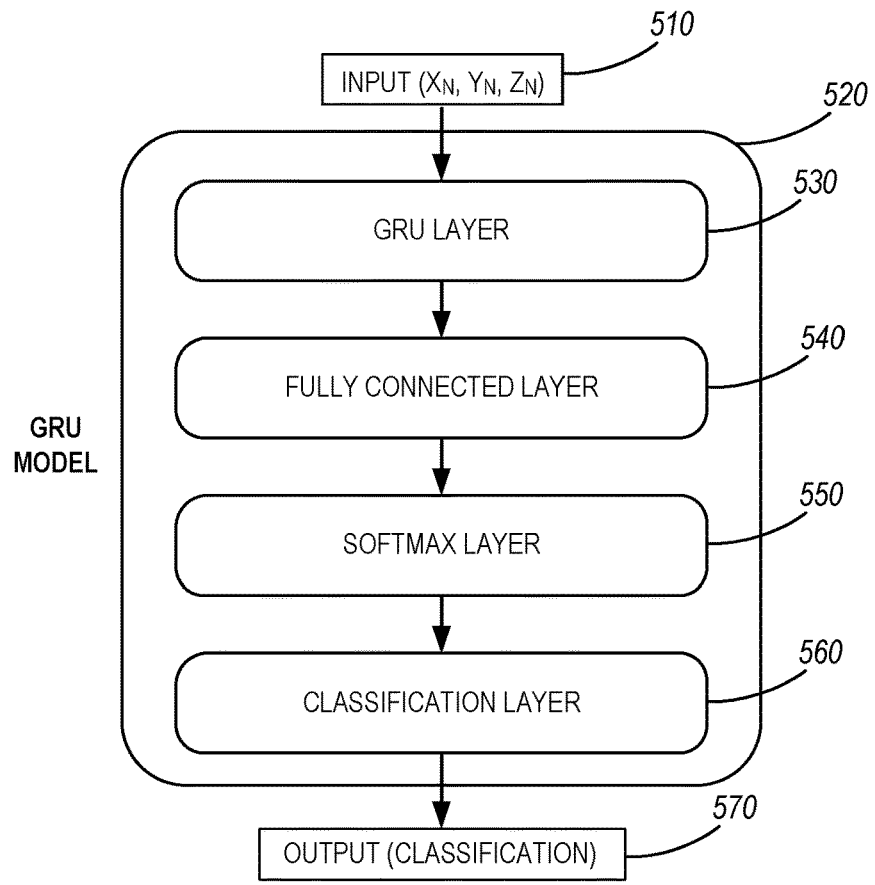
FIG. 5 illustrates a Gated Recurrent Unit (GRU) model architecture, according to an example.

FIG. 5 illustrates a Gated Recurrent Unit (GRU) model architecture. Specifically, this shows the use of a GRU model 520 which includes three layers: a GRU layer 530; a fully connected layer 540; softmax layer 550; and classification layer 560.

A single acc data $X_n=[x_n, y_n, z_n]$ is provided as input 510 into the GRU layer. This input 510 is first standardized by $$\left(X_n = \frac{X_n - \mu}{\sigma}\right),$$

where $\mu$ and $\sigma$ are predetermined standard deviation and mean value of training data, respectively.

For the first time step n=0 and $h_0=0$:

$$z_n = \sigma_{LUT}([W_z X_n]_{LUT} + [R_z h_{n-1}]_{LUT} + b_z)$$

$$r_n = \sigma_{LUT}([W_r X_n]_{LUT} [R_r h_{n-1}]_{LUT} b_r)$$

$$\hat{h}_n = \phi_{LUT}([W_h X_n]_{LUT} r_n \odot [R_h h_{n-1}]_{LUT} b_n)$$

$$h_n = (1-z_n) \odot h_{n-1} + z_n \odot \hat{h}_n \qquad \text{(Equation 1)}$$

Where LUT represents the lookup table for the specified operation or function. At each time step the hidden state $h_n$ contains the output of the GRU layer.

Figure 6:
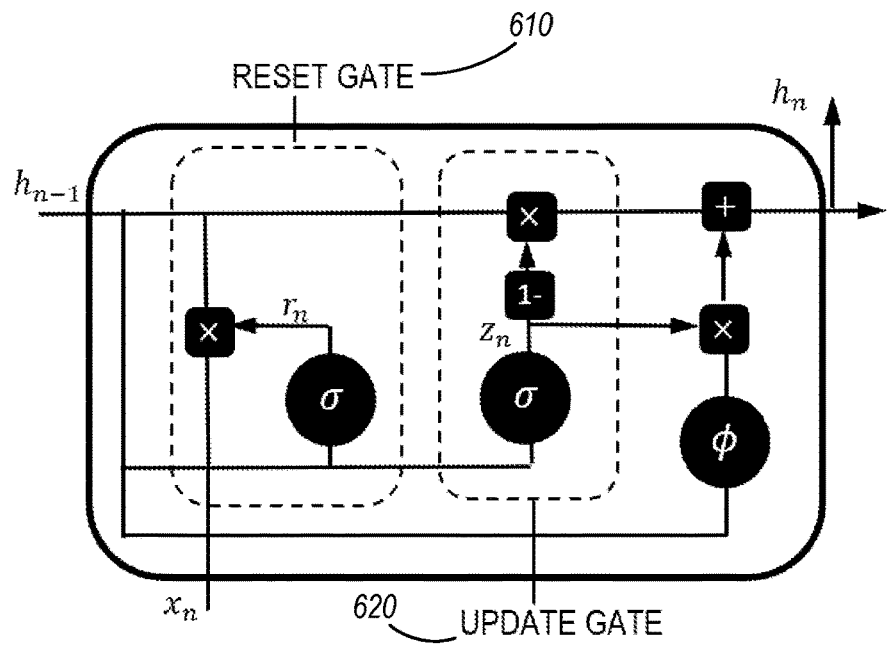
FIG. 6 illustrates a schematic of a Gated Recurrent Unit (GRU) layer, according to an example.

FIG. 6 illustrates a more detailed schematic of a Gated Recurrent Unit (GRU) layer, such as corresponding to the GRU layer 530. The learned weights of the GRU are the input weights $W=[W_z, W_r, W_h]$, the recurrent weights $R=[R_z, R_r, R_h]$ and the bias $b=[b_z, b_r, b_h]$. $\odot$ denotes the elementwise multiplication. $r_n$ and $z_n$ are reset gate 610 and update gate 620 respectively. $\hat{h}_n$ is the candidate state and determines the level of information to be added to the hidden state.

The output of the GRU layer 530 will then send to a fully connected layer 540 which transforms the GRU layer output to the class label dimensions:

$$\text{score}=[\text{score}_{fall}, \text{score}_{nonfall}]=[W_{full} * H]_{LUT} + b_{full} \qquad \text{(Equation 2)}$$

Here, $W_{full}$ and $b_{full}$ are predefined input weights and bias matrices of fully connected layer. LUT represents look up table for the matrix multiplication operation and H is the output of the GRU layer 530. score is a two-dimensional vector containing the scores of fall ($\text{score}_{fall}$) and non-fall ($\text{score}_{nonfall}$) labels.

Returning to FIG. 5, the output of fully connected layer 540 is then provided to a softmax layer 550:

$$C_i = \frac{\exp(\text{score}_i)}{\exp(\text{score}_{fall}) + \exp(\text{score}_{nonfall})} \quad \text{(Equation 3)}$$

Here, i represents either fall or nonfall label and $C_i$ shows the final score label for each class (a number between 0 and 1). Finally, based on the predetermined threshold (a number between 0 and 1), the classification 570 of a current data point is determined.

Figure 7:
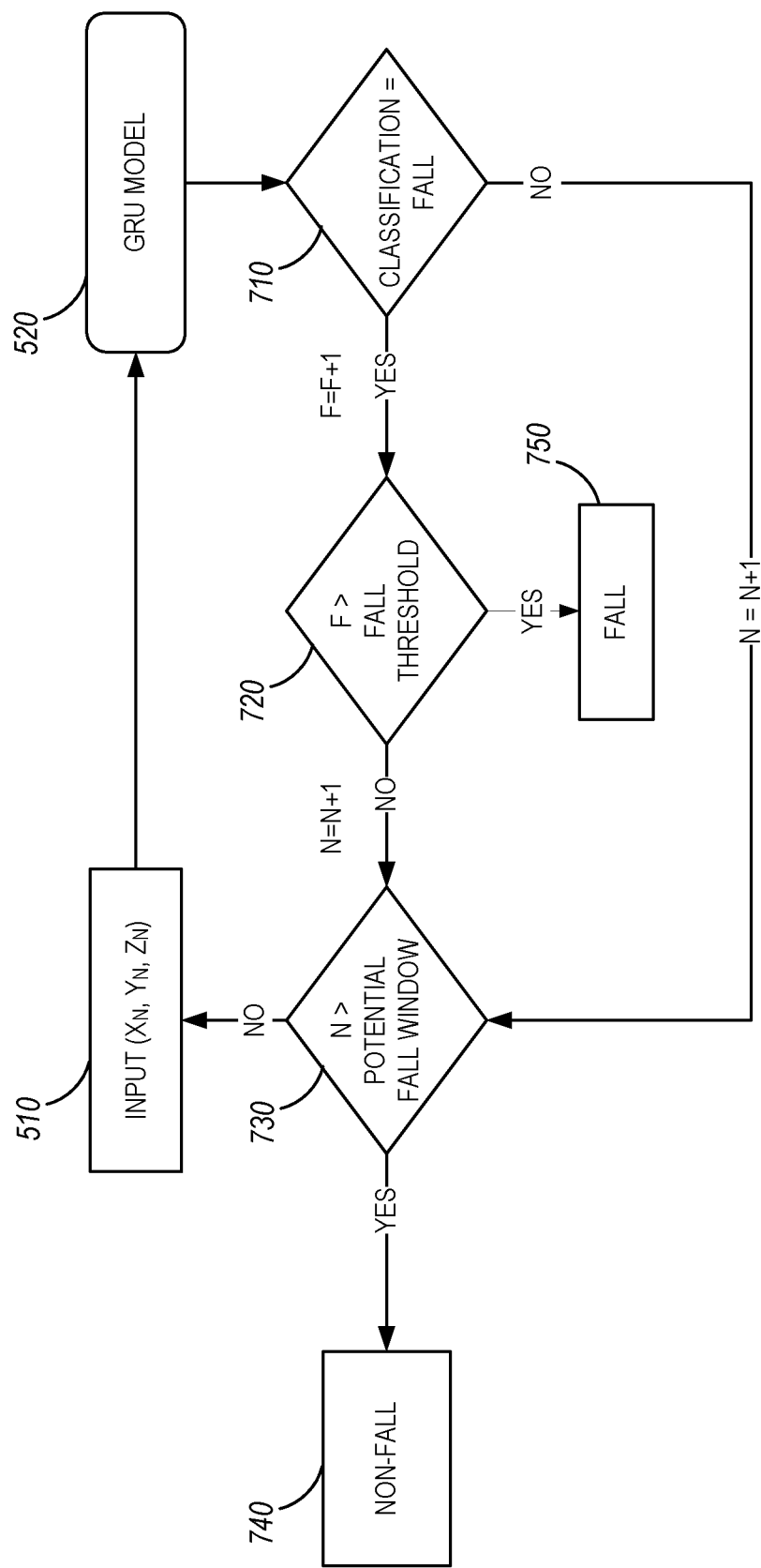
FIG. 7 illustrates a classification processing flowchart for a potential fall window in a Gated Recurrent Unit (GRU) model, according to an example.

FIG. 7 illustrates a classification processing flowchart for a potential fall window in a GRU model. This flowchart specifically shows a scenario where f is the counter for the consecutive fall labels, n is the counter for the number of samples in the potential fall window. This flowchart further shows the results of processing the input 510 with the GRU model 520, and evaluation of whether the classification 570 indicates a fall (evaluation 710).

Here, during the GRU model processing, if the number of consecutive predicted fall labels are greater than a predetermined fall window threshold (evaluation 720) the potential fall window will be labeled as a fall (outcome 750). If the number of consecutive predicted fall labels are not greater than the predetermined fall window threshold (evaluation 720), then an evaluation of the number of samples (evaluation 730) may be used to indicate a non-fall (outcome 740).

Figure 8:
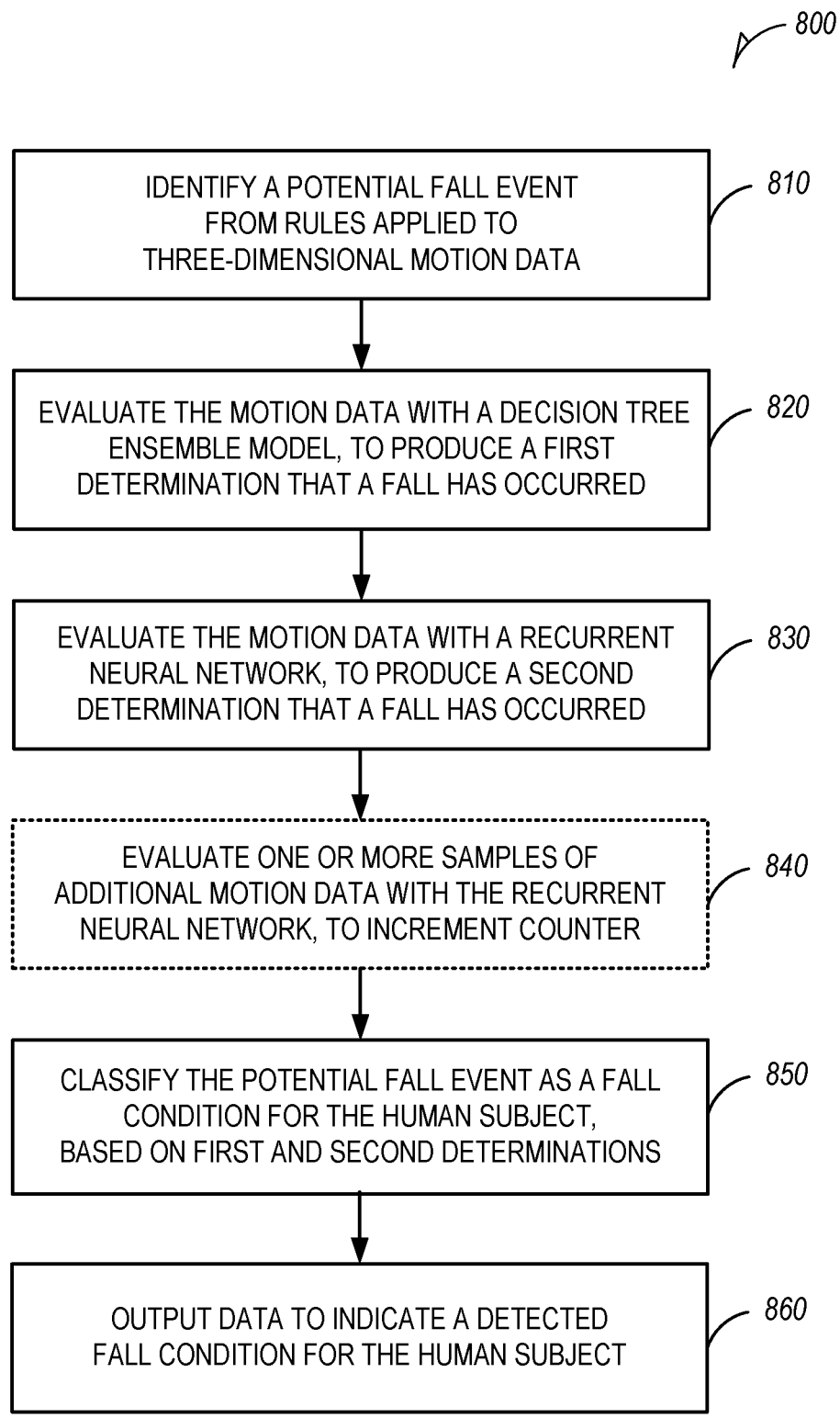
FIG. 8 illustrates a flowchart of a method for fall detection using a hybrid detection algorithm, according to an example.

FIG. 8 illustrates a flowchart 800 of an example method of fall detection using a hybrid detection algorithm, implemented within processing circuitry of a wearable device. It will be understood that this method may be accomplished by programming or logic in configured circuitry of the wearable device, by the execution of device-readable instructions (e.g., from memory or a storage medium) on the circuitry of the wearable device, or other variations of configured software and hardware.

At operation 810, an identification of a potential fall event is performed, using one or more rules that are applied to three-dimensional motion data. In a further example, the sensor is a tri-axial accelerometer, and the motion data is acceleration data from the accelerometer that is down-sampled. Such motion data may be collected for a predefined amount of time, and may provide an ongoing stream of motion data to a data buffer, as discussed above. Also in a further example, the one or more rules relate to acceleration, velocity, or variability of motion. The one or more rules may be applied to the motion data to identify the potential fall event, serving as a filter for the motion data.

At operation 820, the motion data is evaluated with a computationally efficient (lightweight) machine learning model, such as a decision tree ensemble (DTE) model. This evaluation is invoked in response to the rules identifying a potential fall event, and this evaluation produces a first determination of whether a fall has occurred (e.g., a binary classification that the fall has or has not occurred, or a probability that the fall has or has not occurred). In a further example, the decision tree ensemble model is provided from a plurality of decision trees. Further, the decision tree ensemble model may be optimized during model training with Bayesian optimization, such as to perform parameter tuning and feature selection among the plurality of decision trees. Other types of computationally efficient or lightweight algorithms may include a: Support Vector Machine, Linear Regression, etc.

At operation 830, the motion data is evaluated with a deep learning neural network such as a recurrent neural network. This evaluation is invoked in response to the decision tree ensemble model producing the first determination, identifying that a fall has occurred (or is probable to have occurred). This evaluation produces a second determination of whether a fall has occurred (e.g., a binary classification that the fall has or has not occurred, or a probability that the fall has or has not occurred). In a further example, the deep learning neural network is a recurrent neural network such as a gated recurrent unit (GRU) model. In a still further example, such a GRU model is optimized during training using one or more of: data augmentation, down-sampling of data, variation of a number of layers of the GRU model, or adjusting weights used in training of the GRU model. Other types of deep learning neural networks may include other variations of recurrent neural networks, deep reinforcement learning models, long short-term memory (LSTM) networks, etc.

At operation 840, one or more samples of additional motion data are evaluated with the recurrent neural network, after (i.e., subsequent to) evaluation of the motion data with the recurrent neural network performed in operation 830. In this operation 840, a counter is maintained to track consecutive fall determinations from the recurrent neural network. The classification of the potential fall event as a fall condition may be further based on the counter exceeding a threshold.

At operation 850, the potential fall event is classified as a fall condition for the human subject, based on the first determination and the second determination each indicating that the fall has occurred. In a further example, fall verification operations are performed on the potential fall event, such as before the classification is made, or before any indication of the fall condition is output or transmitted to another device. For instance, fall verification may require a lack of activity from the human subject within a period of time after the potential fall event. Other classifications may occur in some scenarios to indicate that a fall has not occurred, or that a fall condition was canceled or cleared.

At operation 860, data is output that indicates the fall condition for the human subject. Also in a further example, a communication is transmitted to a local or remote device or system (e.g., external to the human subject). This communication may include the output data that indicates the fall condition for the human subject, and cause various alert or emergency processing operations to be initiated, controlled, or canceled.

The following provides an overview of machine learning models and computer systems, which may implement the preceding examples. It will be understood that additional functionality, features, and operations may also be provided or extended on these examples.

Figure 9:
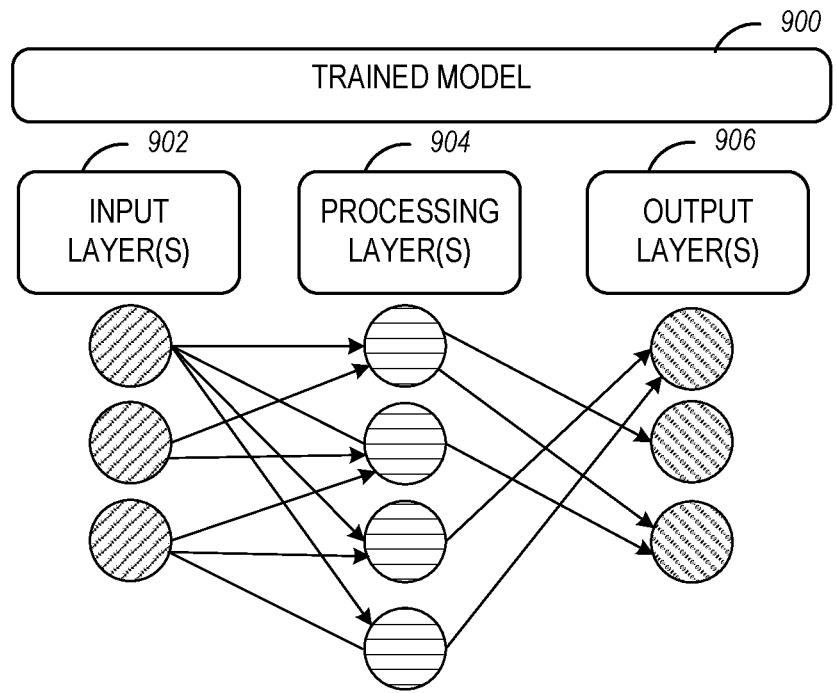
FIG. 9 illustrates a multi-layer model arrangement for processing data, according to an example.

FIG. 9 illustrates an example multi-layer model arrangement provided as part of a trained model 900 (e.g., implemented by a machine learning model discussed herein, etc.). Specifically, FIG. 9 illustrates a multi-layer model example 900, having an inputs layer 902 (e.g., for a first level of data processing), processing layer 904 (e.g., for a second and subsequent level of data processing), and output layer 906 (e.g., for a final level of data processing). In various examples, such a multi-layer model may be used for implementing the machine learning models discussed above. When the model is used to perform an assessment (e.g., to detect that a fall has occurred), new data (e.g., sensor data) is provided as an input to the model, and the model generates the assessment as output.

As will be understood, Machine Learning (ML) is an approach that provides computer systems the ability to perform tasks, without explicitly being programmed, by making inferences based on patterns found in the analysis of data. Machine learning explores the study and construction of algorithms, that may learn from existing data and make predictions about new data. Such machine-learning algorithms operate by building an ML model from example training data in order to make data-driven predictions or decisions expressed as outputs or assessments. Although example embodiments are presented with respect to specific uses of decision tree ensembles and recurrent neural networks, the principles presented herein may be applied to other types and variations of machine-learning models and deep learning neural networks.

In various examples, the ML model may be trained from supervised ML or unsupervised ML techniques. Supervised ML uses prior knowledge (e.g., examples that correlate inputs to outputs or outcomes) to learn the relationships between the inputs and the outputs. The goal of supervised ML is to learn a function that, given some training data, best approximates the relationship between the training inputs and outputs so that the ML model can implement the same relationships when given inputs to generate the corresponding outputs. Unsupervised ML is the training of an ML algorithm using information that is neither classified nor labeled, and allowing the algorithm to act on that information without guidance. Unsupervised ML is useful in exploratory analysis because it can automatically identify structure in data. Supervised ML tasks include classification problems and regression problems. Classification problems, also referred to as categorization problems, aim at classifying items or outcomes into one of several category values (for example, is this object an apple or an orange?). Regression algorithms aim at quantifying some items (for example, by providing a score to the value of some input). Some examples of commonly used supervised-ML algorithms are Logistic Regression (LR), Naive-Bayes, Random Forest (RF), neural networks (NN), deep neural networks (DNN), matrix factorization, and Support Vector Machines (SVM). Unsupervised ML tasks include clustering, representation learning, and density estimation. Some examples of commonly used unsupervised-ML algorithms are K-means clustering, principal component analysis, and autoencoders.

In an example, the training data for a ML model includes examples of values for data features. In some example embodiments, the training data comprises labeled data with examples of values for the features and labels indicating the outcome. The machine-learning algorithms utilize the training data to find correlations among identified features that affect the outcome. A feature is an individual measurable property of a phenomenon being observed. The concept of a feature is related to that of an explanatory variable used in statistical techniques such as linear regression. Choosing informative, discriminating, and independent features is important for effective operation of ML in pattern recognition, classification, and regression. Features may be provided from different types, such as numeric features, strings, and graphs.

During training, the ML algorithm analyzes the training data based on identified features and configuration parameters defined for the training. The result of the training is a trained ML model that is capable of taking inputs to produce assessments (e.g., used in the fall detection processes discussed above). Training an ML algorithm often involves analyzing large amounts of data (e.g., from several megabytes to a terabyte or more) in order to find data correlations.

The ML algorithms utilize the training data to find correlations among the identified features that affect the outcome or assessment. In some example examples, the training data includes labeled data, which is known data for one or more identified features and one or more outcomes (e.g., related to aspects of outcomes for fall detection).

The ML algorithms may explore many possible functions and parameters before finding what the ML algorithms identify to be the best correlations within the data; therefore, training of the ML algorithms may make use of large amounts of computing resources and time. In example embodiments, some ML algorithms may include configuration parameters, and the more complex the ML algorithm, the more parameters there are that are available to the user. The configuration parameters define variables for an ML algorithm in the search for the best ML model. The training parameters therefore may include model parameters and hyperparameters. Model parameters are learned from the training data, whereas hyperparameters are provided to the ML algorithm. Some examples of model parameters include maximum model size, maximum number of passes over the training data, data shuffle type, regression coefficients, decision tree split locations, and the like. Hyperparameters may include the number of hidden layers in a neural network, the number of hidden nodes in each layer, the learning rate (perhaps with various adaptation schemes for the learning rate), the regularization parameters, types of nonlinear activation functions, and the like. Finding the correct (or the best) set of hyperparameters can be a time-consuming task that makes use of a large amount of computer resources.

Based on the foregoing, it will be understood that a variety of customizations for training, configuration, and use of a ML model may be provided. Other implementations of machine learning and artificial intelligence processing may be integrated into the fall detection processes described herein, consistent with the examples above.

Figure 10:
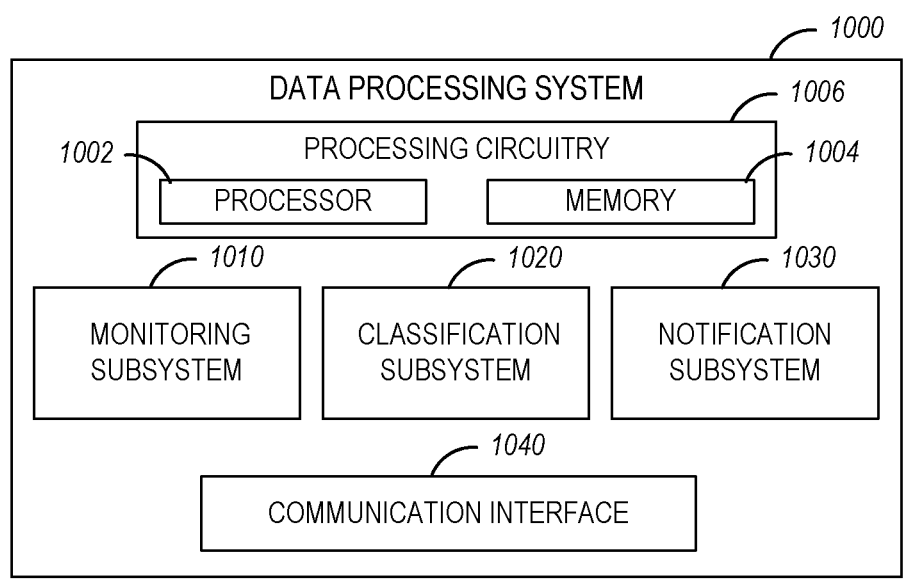
FIG. 10 illustrates a computer system implementation of a data processing system, used for performing any one of the methodologies discussed herein, according to an example.

FIG. 10 illustrates, by way of example, a block diagram of an embodiment of a data processing system 1000 (e.g., a computing system) implementing processing circuitry 1006 to implement the devices or systems herein (e.g., PERS 108). The system 1000 may be operated by and embodied in a number of different computing platforms, such as in a server form factor, a workstation or personal computer form factor, a mobile computing device, etc. In some examples, the system 1000 may be a networked device connected via a network (or combination of networks) to a computing system operating a user interface computing system using a communication interface 1040. The network may include local, short-range, or long-range networks, such as Bluetooth, cellular, IEEE 802.11 (Wi-Fi), or other wired or wireless networks.

The system 1000 includes a processor 1002 and a memory 1004, which can be optionally included as part of processing circuitry 1006. The processor 1002 may be any single processor or group of processors that act cooperatively. The memory 1004 may be any type of memory, including volatile or non-volatile memory. The memory 1004 may include instructions, which when executed by the processor 1002, cause the processor 1002 to implement the features of a monitoring subsystem 1010, classification or algorithm processing subsystem 1020, and a notification subsystem 1030. Thus, the following references to electronic operations in the system 1000 or the processing circuitry 1006 may be performed by the processor 1002 or the circuitry 1006 as a whole. Further, the processor 1002 or circuitry 1006 may implement any of the features of methods 200 or 800 (or similar data processing functions) for identifying and signaling a fall condition, utilizing the algorithms and approaches discussed herein. The processor 1002 or circuitry 1006 may further provide data and commands to assist the processing and implementation of the fall detection approaches using communication interface 1040. It will be understood that the processor 1002 or circuitry 1006 may also implement other aspects of the programming devices and device interfaces described above with reference to the operations of FIGS. 1 to 10.

Figure 11:
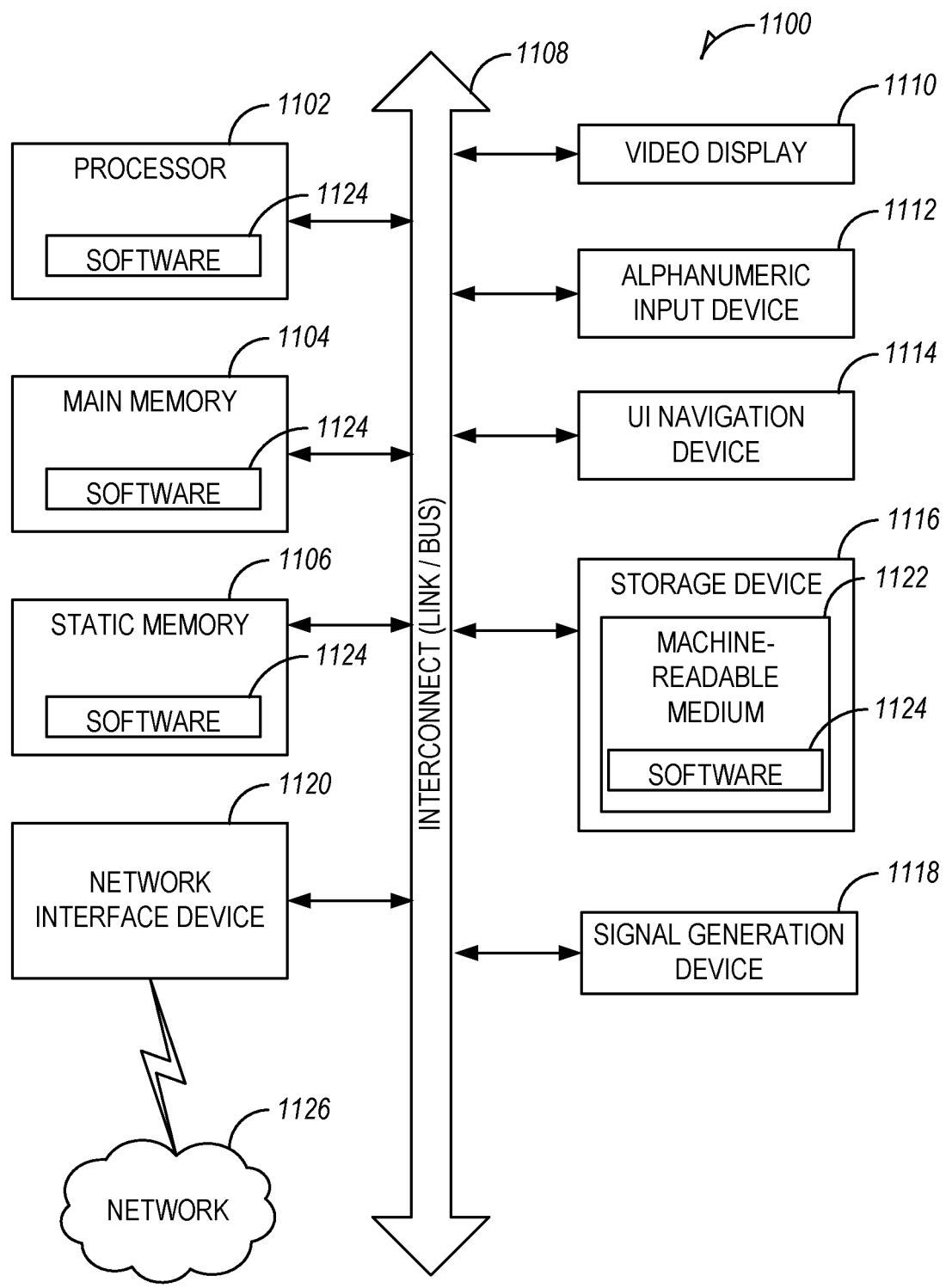
FIG. 11 is a block diagram illustrating a machine in the example form of a computer system, within which a set or sequence of instructions may be executed to cause the machine to perform any one of the methodologies discussed herein, according to an example.

FIG. 11 is a block diagram illustrating a machine in the example form of a computer system 1100, within which a set or sequence of instructions may be executed to cause the machine to perform any one of the methodologies discussed herein, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be a personal computer (PC), a tablet PC, a hybrid tablet, a personal digital assistant (PDA), a mobile telephone, a medical device programmer, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by a processor (e.g., a computer) to individually or jointly execute instructions to perform any one or more of the methodologies discussed herein.

Example computer system 1100 includes at least one processor 1102 (e.g., a central processing unit (CPU), a graphics processing unit (GPU) or both, processor cores, compute nodes, etc.), a main memory 1104 and a static memory 1106, which communicate with each other via an interconnect 1108 (e.g., link or bus). The computer system 1100 may further include a video display unit 1110, an alphanumeric input device 1112 (e.g., a keyboard), and a user interface (UI) navigation device 1114 (e.g., a mouse). In one embodiment, the video display unit 1110, input device 1112 and UI navigation device 1114 are incorporated into a touch screen display. The computer system 1100 may additionally include a storage device 1116 (e.g., a drive unit), a signal generation device 1118 (e.g., a speaker), a network interface device 1120, and one or more sensors (not shown), such as a global positioning system (GPS) sensor, compass, accelerometer, or other sensor. It will be understood that other forms of machines or apparatuses that are capable of implementing the methodologies discussed in this disclosure may not incorporate or utilize every component depicted in FIG. 11 (such as a GPU, video display unit, keyboard, etc.).

The storage device 1116 includes a machine-readable medium 1122 on which is stored one or more sets of data structures and instructions 1124 (e.g., software) embodying or utilized by any one or more of the methodologies or functions described herein. The instructions 1124 may also reside, completely or at least partially, within the main memory 1104, static memory 1106, and/or within the processor 1102 during execution thereof by the computer system 1100, with the main memory 1104, static memory 1106, and the processor 1102 also constituting machine-readable media.

While the machine-readable medium 1122 is illustrated in an example embodiment to be a single medium, the term "machine-readable medium" may include a single medium or multiple media (e.g., a centralized or distributed database, and/or associated caches and servers) that store the one or more instructions 1124. The term "machine-readable medium" shall also be taken to include any tangible (e.g., non-transitory) medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions 1124 may further be transmitted or received over a communications network 1126 using a transmission medium via the network interface device 1120 utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., Wi-Fi, 3G, and 4G LTE/LTE-A or 5G networks). The term "transmission medium" shall be taken to include any intangible medium that is capable of storing, encoding, or carrying instructions for execution by the machine, and includes digital or analog communications signals or other intangible medium to facilitate communication of such software.

What is claimed is:

1. A device, comprising:
   a sensor configured to obtain three-dimensional motion data of a human subject, wherein the motion data includes sensor measurements collected in a subject time period and in an earlier time period before the subject time period; and
   processing circuitry configured to:
   identify a potential fall event from the motion data, based on one or more rules;
   evaluate first samples of the motion data with a machine learning model, to produce a first determination that a fall has occurred during the potential fall event, wherein the first samples correspond to the sensor measurements collected in the subject time period, and wherein use of the machine learning model is invoked in response to the potential fall event identified using the one or more rules;
   evaluate second samples of the motion data with a deep learning neural network, to produce a second determination that a fall has occurred during the potential fall event, wherein use of the deep learning neural network is invoked after the use of the machine learning model, in response to the first determination produced from the machine learning model indicating that the fall has occurred, wherein the second samples correspond to the sensor measurements collected in the subject time period and in the earlier time period;

classify the potential fall event as a fall condition for the human subject, based on the first determination produced from the machine learning model and the second determination produced from the deep learning neural network both indicating that the fall has occurred; and output data to indicate the fall condition for the human subject.

2. The device of claim 1, wherein the sensor is a tri-axial accelerometer, wherein the motion data is acceleration data which is downsampled, and wherein the motion data is collected for a predefined amount of time.

3. The device of claim 1, wherein the one or more rules relate to acceleration, velocity, or variability of motion, wherein the one or more rules are applied to the motion data to identify the potential fall event.

4. The device of claim 1, wherein the machine learning model is a decision tree ensemble model provided from a plurality of decision trees, and wherein the decision tree ensemble model is optimized during training with Bayesian optimization of parameter tuning and feature selection for the plurality of decision trees.

5. The device of claim 1, wherein the deep learning neural network is a gated recurrent unit (GRU) model, wherein the GRU model is optimized during training using one or more of: data augmentation, down-sampling of data, variation of a number of layers of the GRU model, or adjusting weights used in training of the GRU model.

6. The device of claim 1, the processing circuitry further configured to:

evaluate one or more samples of additional motion data with the deep learning neural network, after evaluation of the motion data with the deep learning neural network, wherein the additional motion data includes sensor measurements collected in a later time period after the subject time period;

wherein a counter is maintained to track consecutive fall determinations produced from the deep learning neural network, and wherein classification of the potential fall event as the fall condition for the human subject is further based on the counter exceeding a threshold.

7. The device of claim 1, the processing circuitry further configured to:

perform fall verification of the potential fall event, before indication of the fall condition for the human subject, wherein the fall verification occurs based on a lack of activity from the human subject within a period of time after the potential fall event.

8. The device of claim 1, the processing circuitry further configured to:

transmit a communication to a device external to the human subject, the communication including the data to indicate the fall condition for the human subject.

9. The device of claim 1, wherein the device is a wearable adapted to be worn on a body of the human subject, and wherein the wearable is provided in a form factor provided from among a: watch, bracelet, or pendant.

10. The device of claim 1, wherein the first determination includes a first probability that a fall has occurred, wherein the second determination includes a second probability that a fall has occurred, wherein use of the deep learning neural network is invoked in response to the first probability exceeding a first probability threshold that a fall has occurred, and wherein the potential fall event is classified as a fall condition for the human subject in response to the second probability exceeding a second probability threshold that a fall has occurred.

11. A method for fall detection, performed by processing circuitry of a wearable device, comprising:

receiving three-dimensional motion data of a human subject, wherein the motion data includes sensor measurements collected in a subject time period and in an earlier time period before the subject time period;

identifying a potential fall event from the three-dimensional motion data of the human subject, the potential fall event identified based on one or more rules;

evaluating first samples of the motion data with a machine learning model, to produce a first determination that a fall has occurred during the potential fall event, wherein the first samples correspond to the sensor measurements collected in the subject time period, and wherein use of the machine learning model is invoked in response to the potential fall event identified using the one or more rules;

evaluating second samples of the motion data with a deep learning neural network, to produce a second determination that a fall has occurred during the potential fall event, wherein use of the deep learning neural network is invoked after the use of the machine learning model, in response to the first determination produced from the machine learning model indicating that the fall has occurred, wherein the second samples correspond to the sensor measurements collected in the subject time period and in the earlier time period;

classifying the potential fall event as a fall condition for the human subject, based on the first determination produced from the machine learning model and the second determination produced from the deep learning neural network both indicating that the fall has occurred; and outputting data to indicate the fall condition for the human subject.

12. The method of claim 11, wherein the motion data is provided from a tri-axial accelerometer, wherein the motion data is acceleration data which is downsampled, and wherein the motion data is collected for a predefined amount of time.

13. The method of claim 11, wherein the one or more rules relate to acceleration, velocity, or variability of motion, wherein the one or more rules are applied to the motion data to identify the potential fall event.

14. The method of claim 11, wherein the machine learning model is a decision tree ensemble model provided from a plurality of decision trees, and wherein the decision tree ensemble model is optimized during training with Bayesian optimization of parameter tuning and feature selection for the plurality of decision trees.

15. The method of claim 11, wherein the deep learning neural network is a gated recurrent unit (GRU) model, wherein the GRU model is optimized during training using one or more of: data augmentation, down-sampling of data, variation of a number of layers of the GRU model, or adjusting weights used in training of the GRU model.

16. The method of claim 11, further comprising:

evaluating one or more samples of additional motion data with the deep learning neural network, after evaluation of the motion data with the deep learning neural network, wherein the additional motion data includes sensor measurements collected in a later time period after the subject time period;

wherein a counter is maintained to track consecutive fall determinations produced from the deep learning neural network, and wherein classification of the potential fall event as the fall condition for the human subject is further based on the counter exceeding a threshold.

17. The method of claim 11, further comprising:
performing fall verification of the potential fall event, before indication of the fall condition for the human subject, wherein the fall verification occurs based on a lack of activity from the human subject within a period of time after the potential fall event.

18. The method of claim 11, further comprising:
transmitting a communication to a device external to the human subject, the communication including the data to indicate the fall condition for the human subject.

19. The method of claim 11, wherein the first determination includes a first probability that a fall has occurred, wherein the second determination includes a second probability that a fall has occurred, wherein use of the deep learning neural network is invoked in response to the first probability exceeding a first probability threshold that a fall has occurred, and wherein the potential fall event is classified as a fall condition for the human subject in response to the second probability exceeding a second probability threshold that a fall has occurred.

20. A non-transitory device-readable storage medium, the device-readable storage medium comprising instructions that, when executed by processor circuitry of an electronic device, causes the electronic device to perform operations that:
receive three-dimensional motion data of a human subject, wherein the motion data includes sensor measurements collected in a subject time period and in an earlier time period before the subject time period;
identify a potential fall event from the three-dimensional motion data of the human subject, the potential fall event identified based on one or more rules;
evaluate first samples of the motion data with a machine learning model, to produce a first determination that a fall has occurred during the potential fall event, wherein the first samples correspond to the sensor measurements collected in the subject time period, and wherein use of the machine learning model is invoked in response to the potential fall event identified using the one or more rules;
evaluate second samples of the motion data with a deep learning neural network, to produce a second determination that a fall has occurred during the potential fall event, wherein use of the deep learning neural network is invoked after the use of the machine learning model, in response to the first determination produced from the machine learning model indicating that the fall has occurred, wherein the second samples correspond to the sensor measurements collected in the subject time period and in the earlier time period;
classify the potential fall event as a fall condition for the human subject, based on the first determination produced from the machine learning model and the second determination produced from the deep learning neural network both indicating that the fall has occurred; and
output data to indicate the fall condition for the human subject.

21. The device-readable storage medium of claim 20, wherein the motion data is provided from a tri-axial accelerometer, wherein the motion data is acceleration data which is downsampled, and wherein the motion data is collected for a predefined amount of time.

22. The device-readable storage medium of claim 20, wherein the one or more rules relate to acceleration, velocity, or variability of motion, wherein the one or more rules are applied to the motion data to identify the potential fall event.

23. The device-readable storage medium of claim 20, wherein the machine learning model is a decision tree ensemble model provided from a plurality of decision trees, and wherein the decision tree ensemble model is optimized during training with Bayesian optimization of parameter tuning and feature selection for the plurality of decision trees.

24. The device-readable storage medium of claim 20, wherein the deep learning neural network is a gated recurrent unit (GRU) model, wherein the GRU model is optimized during training using one or more of: data augmentation, down-sampling of data, variation of a number of layers of the GRU model, or adjusting weights used in training of the GRU model.

25. The device-readable storage medium of claim 20, the instructions further to cause the electronic device to perform operations that:
evaluate one or more samples of additional motion data with the deep learning neural network, after evaluation of the motion data with the deep learning neural network, wherein the additional motion data includes sensor measurements collected in a later time period after the subject time period;
wherein a counter is maintained to track consecutive fall determinations produced from the deep learning neural network, and wherein classification of the potential fall event as the fall condition for the human subject is further based on the counter exceeding a threshold.

26. The device-readable storage medium of claim 20, the instructions further to cause the electronic device to perform operations that:
perform fall verification of the potential fall event, before indication of the fall condition for the human subject, wherein the fall verification occurs based on a lack of activity from the human subject within a period of time after the potential fall event.

27. The device-readable storage medium of claim 20, the instructions further to cause the electronic device to perform operations that:
transmit a communication to a device external to the human subject, the communication including the data to indicate the fall condition for the human subject.

28. The device-readable storage medium of claim 20, wherein the first determination includes a first probability that a fall has occurred, wherein the second determination includes a second probability that a fall has occurred, wherein use of the deep learning neural network is invoked in response to the first probability exceeding a first probability threshold that a fall has occurred, and wherein the potential fall event is classified as a fall condition for the human subject in response to the second probability exceeding a second probability threshold that a fall has occurred.

* * * * *